United States Patent
Quallich et al.

(10) Patent No.: US 6,825,193 B2
(45) Date of Patent: Nov. 30, 2004

(54) CITRIC ACID SALT OF A THERAPEUTIC COMPOUND AND PHARMACEUTICAL COMPOSITIONS THEREOF

(75) Inventors: George J. Quallich, North Stonington, CT (US); Lewin T. Wint, Wilmette, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/313,467

(22) Filed: Dec. 6, 2002

(65) Prior Publication Data

US 2003/0181444 A1 Sep. 25, 2003

Related U.S. Application Data

(60) Provisional application No. 60/338,343, filed on Dec. 7, 2001.

(51) Int. Cl.[7] ..................... A61K 31/541; C07D 417/10
(52) U.S. Cl. ..................... 514/227.8; 544/58.2
(58) Field of Search ..................... 544/58.2; 514/227.8

(56) References Cited

U.S. PATENT DOCUMENTS 6,380,186 B1 * 4/2002 Howard ................... 514/227.8

6,423,708 B1 * 7/2002 Gibbs et al. ................ 514/227.8

FOREIGN PATENT DOCUMENTS

| WO | WO 9814433 | 4/1998 |
| WO | WO 0246167 | 6/2002 |

* cited by examiner

*Primary Examiner*—Richard L. Raymond
(74) *Attorney, Agent, or Firm*—Peter C. Richardson; A. David Joran; Lorraine B. Ling

(57) ABSTRACT

The present invention is directed to a polymorph of the citrate salt of 4-(3,4-dichlorophenyl)-2-[2-(4-methylpiperazin-1-yl)-benzylidene]-thiomorpholin-3-one:

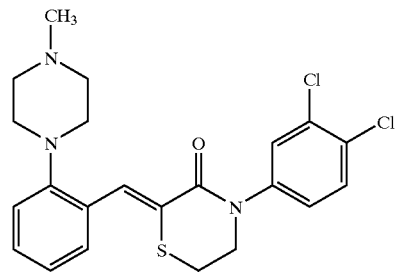

and pharmaceutical compositions thereof.

3 Claims, 5 Drawing Sheets

CITRIC ACID SALT OF A THERAPEUTIC COMPOUND AND PHARMACEUTICAL COMPOSITIONS THEREOF

REFERENCE TO RELATED APPLICATION

This application claims benefit of provisional application No. 60/338,343 filed Dec. 7, 2001

The present invention is directed to a polymorph of the citric acid salt of 4-(3,4-dichlorophenyl)-2-[2-(4-methylpiperazin-1-yl)-benzylidene]-thiomorpholin-3-one:

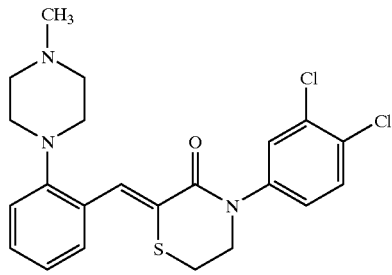

and pharmaceutical compositions thereof.

The compound, 4-(3,4-dichlorophenyl)-2-[2-(4-methylpiperazin-1-yl )-benzylidene]-thiomorpholin-3-one, is an antagonist of the serotonin-1D (5-HT$_{1D}$) receptor and is useful in the treatment of a number of disorders, diseases and conditions of the central nervous system. This compound is particularly useful in the treatment of hypertension, all forms of depression, depression in cancer patients, depression in Parkinson's patients, postmyocardial infarction depression, subsyndromal symptomatic depression, depression in infertile women, pediatric depression, major depressive disorder, single episode depression, recurrent depression, child abuse induced depression, post partum depression, dysthymia; mild, moderate, or severe depressions with or without atypical features, melancholic features, psychotic features, catatonic features; seasonal affective disorder, geriatric depression, chronic depression; adjustment disorder with depressed mood or with anxiety and depressed mood; mixed anxiety and depression; substance induced mood disorder; and mood disorder secondary to a general medical condition, bipolar disorder, bipolar disorder-depressed phase, generalized anxiety disorder, phobias, agoraphobia, social anxiety, social phobia, simple phobias, separation anxiety disorder, posttraumatic stress syndrome, avoidant personality disorder, premature ejaculation, eating disorders, binge eating disorder, anorexia nervosa, bulimia nervosa, obesity; chemical dependencies and addictions to alcohol, cocaine, heroin, phenobarbital, nicotine, marijuana and benzodiazepines; cluster headache, migraine, pain, Alzheimer's disease, obsessive-compulsive disorder, panic disorder, panic disorder with agoraphobia, memory disorders, dementia, amnestic disorders, and age-related cognitive decline (ARCD), Parkinson's diseases, dementia in Parkinson's disease, neuroleptic-induced parkinsonism and tardive dyskinesias, endocrine disorders, hyperprolactinaemia, vasospasm, vasospasm in the cerebral vasculature, cerebellar ataxia; gastrointestinal tract disorders involving changes in motility and secretion; negative symptoms of schizophrenia, premenstrual syndrome, fibromyalgia syndrome, stress incontinence, Tourette's syndrome, trichotillomania, kleptomania, male impotence, cancer, small cell lung carcinoma, chronic paroxysmal hemicrania, headache associated with vascular disorders, autism, pervasive developmental disorder NOS, Asperger's disorder, selective mutism, chronic motor or vocal tic disorder, somatization disorder, insomnia, intermittent explosive disorder, pyromania, pathological gambling, impulse-control disorder, premenstrual dysphoric disorder and attention-deficit/hyperactivity disorder (ADHD) in a mammal, particularly a human. The citrate salt of this invention may also be used in a pharmaceutical composition in combination with a serotonin reuptake inhibiting antidepressant (SRI), in order to treat a number of these conditions.

Compounds that are antagonists of the serotonin-1D receptor, including 4-(3,4-dichlorophenyl)-2-[2-(4-methylpiperazin-1-yl)-benzylidene]-thiomorpholin-3-one, specifically including its hydrochloride salt, are referred to in WO 98/14433, published Apr. 9, 1998 (corresponding to U.S. Ser. No. 09/254,999, filed Oct. 8, 1999, now U.S. Pat. No. 6,380,186, Ser. No. 09/733346, filed Dec. 8, 2000, now U.S. Pat. No. 6,423,708 and PCT/IB01/02139, filed Nov. 12, 2001). The foregoing applications, owned in common with the present application and incorporated herein by reference in their entirety, generically recite pharmaceutically acceptable acid addition salts for the compounds referred to therein.

The citrate salt of the present invention exhibits properties, including those of solid-state stability and compatibility with certain drug product formulation excipients, that render it superior to previously known salts of 4-(3,4-dichlorophenyl)-2-[2-(4-methylpiperazin-1-yl)-benzylidene]-thiomorpholin-3-one.

SUMMARY OF THE INVENTION

Figure 1:
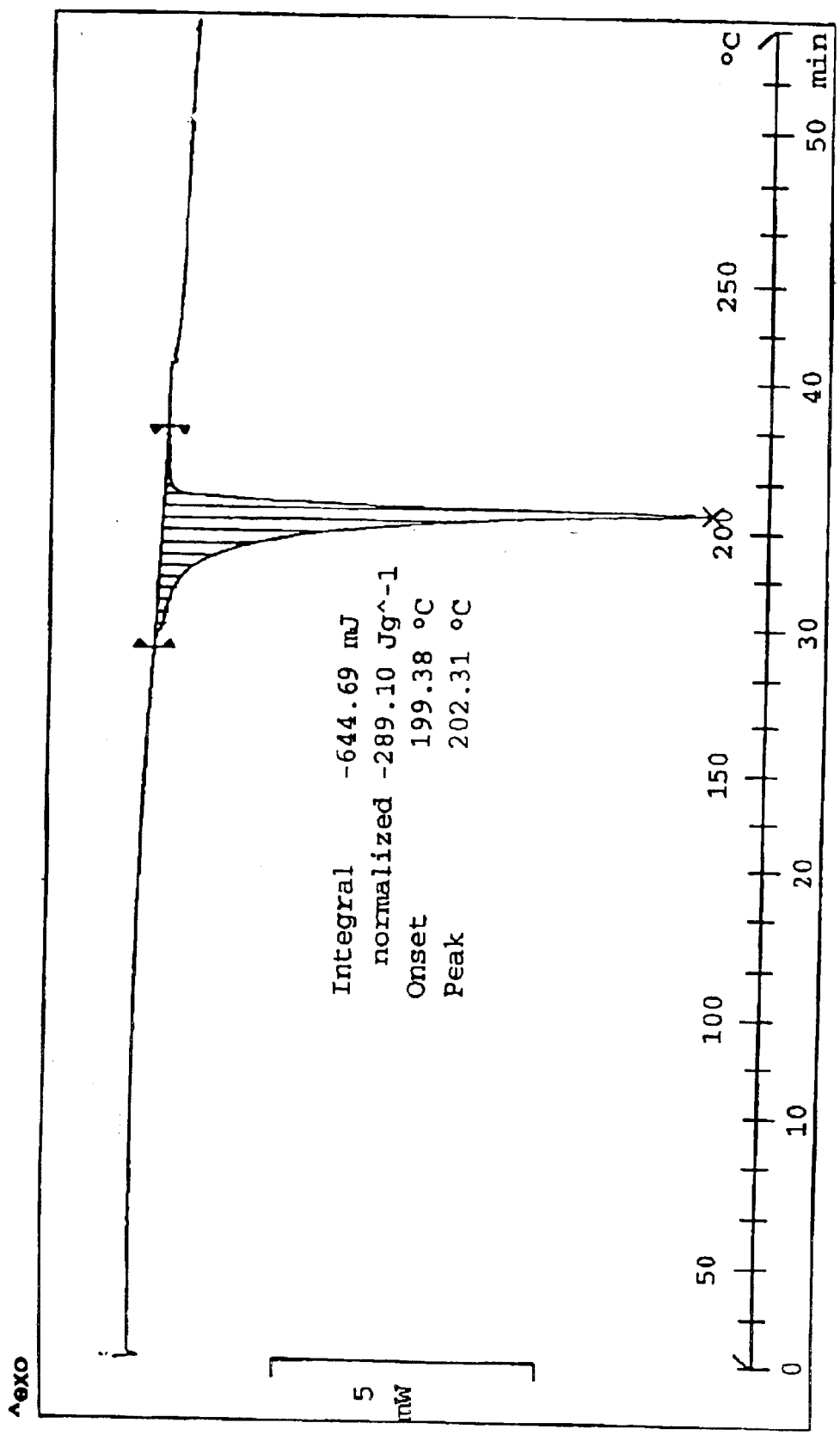
FIG. 1 is the differential scanning calorimetric (DSC) trace of the citrate salt of 4-(3,4-dichlorophenyl)-2-[2-(4-methylpiperazin-1-yl)-benzylidene]-thiomorpholin-3-one.

The present invention relates to the citrate salt of 4-(3,4-dichlorophenyl)-2-[2-(4-methylpiperazin-1-yl)-benzylidene]-thiomorpholin-3-one. The citrate salt of the invention is an anhydrous or nearly anhydrous polymorph.

This citrate salt of the invention is further characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 13.0 | 6.8 |
| 17.4 | 5.1 |
| 18.0 | 4.9 |
| 18.9 | 4.7 |
| 20.0 | 4.4 |
| 21.2 | 4.2 |
| 22.2 | 4.0 |
| 24.0 | 3.7 |
| 27.1 | 3.3 |
| 32.4 | 2.8 |

The citrate salt of the invention is characterized in that it generally forms flakes. Further, the citrate salt is also characterized in that it forms monoclinic crystals belonging to the Pc space group. The citrate salt is further characterized in having an onset of melting transition/decomposition point at about 198–199° C. as measured by differential scanning calorimetry (DSC). Further, the citrate salt of the invention is also characterized in having an aqueous solubility of 1.3 mg/ml and a native pH of 3.37 in aqueous solution. In addition, the citrate salt has a hygroscopicity of approximately 1.27% at 90% relative humidity.

The citrate salt of the invention is also characterized in that when examined by solid state $^{13}$C NMR cross-polarization magic angle spinning techniques it exhibits the following principal resonance peaks downfield from 100 parts per million (±0.1 ppm; relative to an adamantane standard at 29.5 ppm): δ 179.3, 177.0, 171.6, 164.0, 151.0 and 144.1.

Another embodiment of the invention relates to a pharmaceutical composition comprising the citrate salt of 4-(3,4-dichlorophenyl)-2-[2-(4-methylpiperazin-1-yl)-benzylidene]-thiomorpholin-3-one, and a pharmaceutically acceptable carrier or excipient, particularly, one for use in the treatment of hypertension, all forms of depression, depression in cancer patients, depression in Parkinson's patients, postmyocardial infarction depression, subsyndromal symptomatic depression, depression in infertile women, pediatric depression, major depressive disorder, single episode depression, recurrent depression, child abuse induced depression, post partum depression, dysthymia; mild, moderate, or severe depressions with or without atypical features, melancholic features, psychotic features, catatonic features; seasonal affective disorder, geriatric depression, chronic depression; adjustment disorder with depressed mood or with anxiety and depressed mood; mixed anxiety and depression; substance induced mood disorder; and mood disorder secondary to a general medical condition, bipolar disorder, bipolar disorder-depressed phase, generalized anxiety disorder, phobias, agoraphobia, social anxiety, social phobia, simple phobias, separation anxiety disorder, post-traumatic stress syndrome, avoidant personality disorder, premature ejaculation, eating disorders, binge eating disorder, anorexia nervosa, bulimia nervosa, obesity; chemical dependencies and addictions to alcohol, cocaine, heroin, phenobarbital, nicotine, marijuana and benzodiazepines; cluster headache, migraine, pain, Alzheimer's disease, obsessive-compulsive disorder, panic disorder, panic disorder with agoraphobia, memory disorders, dementia, amnestic disorders, and age-related cognitive decline (ARCD), Parkinson's diseases, dementia in Parkinson's disease, neuroleptic-induced parkinsonism and tardive dyskinesias, endocrine disorders, hyperprolactinaemia, vasospasm, vasospasm in the cerebral vasculature, cerebellar ataxia; gastrointestinal tract disorders involving changes in motility and secretion; negative symptoms of schizophrenia, premenstrual syndrome, fibromyalgia syndrome, stress incontinence, Tourette's syndrome, trichotillomania, kleptomania, male impotence, cancer, small cell lung carcinoma, chronic paroxysmal hemicrania, headache associated with vascular disorders, autism, pervasive developmental disorder NOS, Asperger's disorder, selective mutism, chronic motor or vocal tic disorder, somatization disorder, insomnia, intermittent explosive disorder, pyromania, pathological gambling, impulse-control disorder, premenstrual dysphoric disorder and attention-deficit/hyperactivity disorder (ADHD) in a mammal, preferably a human.

The present invention further relates to a the method of treating hypertension, all forms of depression, depression in cancer patients, depression in Parkinson's patients, postmyocardial infarction depression, subsyndromal symptomatic depression, depression in infertile women, pediatric depression, major depressive disorder, single episode depression, recurrent depression, child abuse induced depression, post partum depression, dysthymia; mild, moderate, or severe depressions with or without atypical features, melancholic features, psychotic features, catatonic features; seasonal affective disorder, geriatric depression, chronic depression; adjustment disorder with depressed mood or with anxiety and depressed mood; mixed anxiety and depression; substance induced mood disorder; and mood disorder secondary to a general medical condition, bipolar disorder, bipolar disorder-depressed phase, generalized anxiety disorder, phobias, agoraphobia, social anxiety, social phobia, simple phobias, separation anxiety disorder, post-traumatic stress syndrome, avoidant personality disorder, premature ejaculation, eating disorders, binge eating disorder, anorexia nervosa, bulimia nervosa, obesity; chemical dependencies and addictions to alcohol, cocaine, heroin, phenobarbital, nicotine, marijuana and benzodiazepines; cluster headache, migraine, pain, Alzheimer's disease, obsessive-compulsive disorder, panic disorder, panic disorder with agoraphobia, memory disorders, dementia, amnestic disorders, and age-related cognitive decline (ARCD), Parkinson's diseases, dementia in Parkinson's disease, neuroleptic-induced parkinsonism and tardive dyskinesias, endocrine disorders, hyperprolactinaemia, vasospasm, vasospasm in the cerebral vasculature, cerebellar ataxia; gastrointestinal tract disorders involving changes in motility and secretion; negative symptoms of schizophrenia, premenstrual syndrome, fibromyalgia syndrome, stress incontinence, Tourette's syndrome, trichotillomania, kleptomania, male impotence, cancer, small cell lung carcinoma, chronic paroxysmal hemicrania, headache associated with vascular disorders, autism, pervasive developmental disorder NOS, Asperger's disorder, selective mutism, chronic motor or vocal tic disorder, somatization disorder, insomnia, intermittent explosive disorder, pyromania, pathological gambling, impulse-control disorder, premenstrual dysphoric disorder and attention-deficit/hyperactivity disorder (ADHD) in a mammal, preferably a human, comprising the administration of the citrate salt of 4-(3,4-dichlorophenyl)-2-[2-(4-methylpiperazin-1-yl)-benzylidene]-thiomorpholin-3-one to the subject in need thereof.

The invention also relates to a process for the preparation of the citrate salt of 4-(3,4-dichlorophenyl)-2-[2-(4-methylpiperazin-1-yl)-benzylidene]-thiomorpholin-3-one comprising the steps of (i) contacting 4-(3,4-dichlorophenyl)-2-[2-(4-methylpiperazin-1-yl)-benzylidene]-thiomorpholin-3-one dissolved in a suitable solvent with citric acid; and (ii) collecting the crystals formed.

A preferred embodiment is wherein the suitable solvent is selected from the group consisting of a $(C_1-C_6)$alkyl alcohol, a $(C_1-C_6)$alkyl ketone or a $(C_1-C_6)$alkyl ether. More preferably, the suitable solvent is 2-propanol. Preferably, the process of the invention is wherein the contacting of step (i) is carried out by contacting 4-(3,4-dichlorophenyl)-2-[2-(4-methylpiperazin-1-yl)-benzylidene]-thiomorpholin-3-one in solution phase with a solution of citric acid. More preferably, contacting of step (i) is carried out by adding solid citric acid to the solution of 4-(3,4-dichlorophenyl)-2-[2-(4-methylpiperazin-1-yl)-benzylidene]-thiomorpholin-3-one.

Preferably, the contacting step is carried out over a period of between 1 and 24 hours, more preferably between 10 and 20 hours, and comprising stirring or mixing the resulting mixture. A preferred embodiment of the process is wherein step (i) is run between ambient temperature and the refluxing temperature of the solvent; more preferably, between ambient temperature and the refluxing temperature of 2-propanol, i.e., about 80° C.; most preferably, the process in run between 30 and 60° C. Preferably, the reaction mixture is allowed to cool to ambient temperature once the addition of citric acid is complete and permitted to stir for the remainder of the reaction period.

The present invention also relates to the citric acid salt of 4-(3,4-dichlorophenyl)-2-[2-(4-methylpiperazin-1-yl)-benzylidene]-thiomorpholin-3-one, prepared in accordance with the process of the invention.

DETAILED DESCRIPTION OF THE INVENTION

The compound, 4-(3,4-dichlorophenyl)-2-[2-(4-methylpiperazin-1-yl)-benzylidene]-thiomorpholin-3-one is an antagonist of the serotonin-1D receptor (5-HT$_{1D}$ receptor) and useful in the treatment of a number of CNS diseases, disorders and conditions. The free base of the compound and its hydrochloride salt may be prepared in accordance with the methods set forth in International Patent Publication No. WO 98/14433, published Apr. 9, 1998 herein incorporated by reference in its entirety.

The citrate salt may be prepared under a variety of different conditions. However, in accordance with the present invention, the free base of 4-(3,4-dichlorophenyl)-2-[2-(4-methylpiperazin-1-yl)-benzylidene]-thiomorpholin-3-one is preferably dissolved in a suitable solvent until completely dissolved, whereupon citric acid is added to the solution thereby prepared to create the citrate addition salt of the invention. Preferably, the suitable solvent is selected from the group consisting of a $(C_1-C_6)$alkyl alcohol, a $(C_1-C_6)$alkyl ketone or a $(C_1-C_6)$alkyl ether; more preferably, a $(C_1-C_6)$alkyl alcohol; most preferably 2-propanol. Preferably, the process of the invention is wherein the contacting of step (i) is carried out by contacting 4-(3,4-dichlorophenyl)-2-[2-(4-methylpiperazin-1-yl)-benzylidene]-thiomorpholin-3-one in solution phase with either a solution of citric acid or the solid form of citric acid.

Preferably, the contacting step is carried out over a period of between 1 and 24 hours, more preferably between 10 and 20 hours, and comprising stirring or mixing the resulting mixture. A preferred embodiment of the process is wherein step (i) is run between ambient temperature and the refluxing temperature of the solvent; more preferably, between ambient temperature and the refluxing temperature of 2-propanol, i.e., about 80° C.; most preferably, the process in run between 30 and 60° C. Preferably, the reaction mixture is allowed to cool to ambient temperature once the addition of citric acid is complete and permitted to stir for the remainder of the reaction period.

The citrate salt of 4-(3,4-dichlorophenyl)-2-[2-(4-methylpiperazin-1-yl)-benzylidene]-thiomorpholin-3-one is only slightly hygroscopic and has high aqueous solubility. These characteristics combined with its relative inertness towards common excipients used in pharmaceutical formulation make it highly suitable for pharmaceutical formulation use.

Although in general the known acid addition salts of 4-(3,4-dichlorophenyl)-2-[2-(4-methylpiperazin-1-yl)-benzylidene]-thiomorpholin-3-one are all crystalline, the majority of those salts are so hygroscopic as to render them poor candidates for pharmaceutical formulation use. The citrate salt of the present invention exhibits a hygroscopicity of approximately 1.27% wt/wt on exposure to 90% relative humidity in a moisture chamber. The aqueous solubility of the citrate salt is 1.3 mg/ml having a pH of 3.37. Further, the citrate salt of 4-(3,4-dichlorophenyl)-2-[2-(4-methylpiperazin-1-yl)-benzylidene]-thiomorpholin-3-one exhibits excellent solid state stability both in light and elevated temperatures as well as high humidity challenges.

Differential Scanning Calorimetry

The solid state thermal behavior of the citrate salt of the invention was investigated by differential scanning calorimetry (DSC). The trace for the salt is shown in FIG. 1. The DSC thermograms were obtained on a Mettler Toledo DSC 821$^e$ (STAR$^e$ System). Generally, samples between 1 and 10 mg were prepared in crimped aluminum pans with a small pinhole. The measurements were run at a heating rate of 5° C. per minute in the range of 30 to 300° C.

As seen in FIG. 1, the citrate salt exhibits onset of melt transition at about 198–199° C. One of skill in the art will however note that in DSC measurement there is a certain degree of variability in actual measured onset and peak temperatures which occur depending on rate of heating, crystal shape and purity, and other measurement parameters.

Powder X-Ray Diffraction Patterns

The power x-ray diffraction patterns for the citrate salt of the invention was collected using a Bruker D5000 diffractometer (Bruker AXS, Madison, Wis.) equipped with copper radiation CuK$_α$, fixed slits (1.0, 1.0, 0.6 mm), and a Kevex solid state detector. Data was collected from 3.0 to 40.0 degrees in two theta (2θ) using a step size of 0.04 degrees and a step time of 1.0 seconds.

The x-ray powder diffraction pattern of the citrate salt was conducted with a copper anode with wavelength 1 at 1.54056 and wavelength 2 at 1.54439 (relative intensity: 0.500). The range for 2θ was between 3.0 to 40.0 degrees with a step size of 0.04 degrees, a step time of 1.00 second, a smoothing width of 0.300 and a threshold of 1.0.

Figure 2:
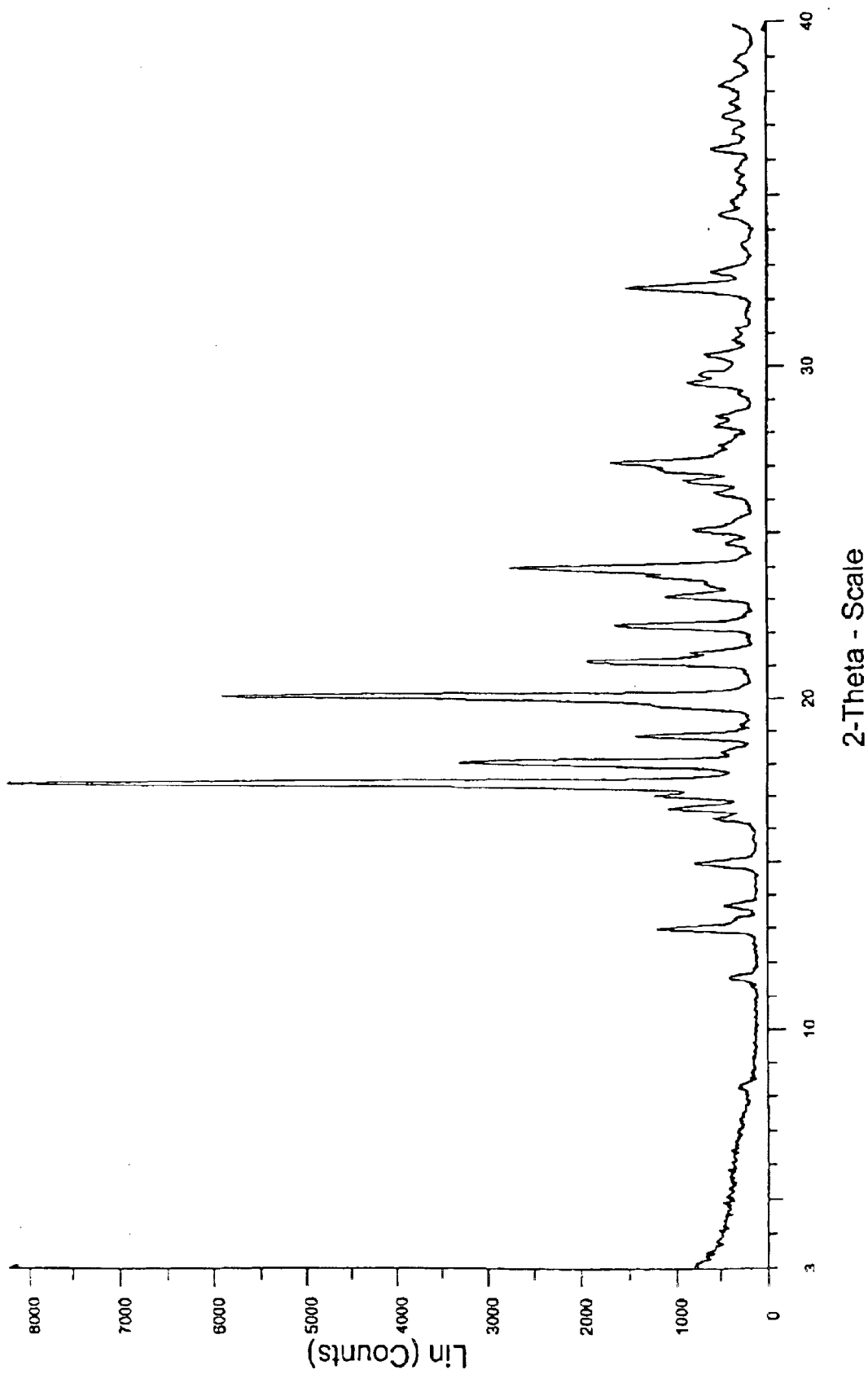
FIG. 2 is the observed powder X-ray diffraction pattern of the citrate salt of 4-(3,4-dichlorophenyl)-2-[2-(4-methylpiperazin-1-yl)-benzylidene]-thiomorpholin-3-one (y axis is linear counts per second; X in degrees 2 theta).

The diffraction peaks at diffraction angles (2θ) in a measured powder X-ray diffraction analysis for the salt are shown in Table I. The relative intensities, however, may change depending on the crystal size and morphology. The actual measured powder diffractogram is displayed in FIG. 2.

TABLE I

Powder X-ray Diffraction Pattern for Citrate Salt with Intensities and Peak Locations of Diffraction Lines.

| Angle 2θ | d-value (Å) | I (rel.) |
|---|---|---|
| 8.2 | 10.7 | 3.7 |
| 11.5 | 7.7 | 4.9 |
| 13.0 | 6.8 | 14.5 |
| 13.7 | 6.5 | 5.6 |
| 14.9 | 5.9 | 9.8 |
| 16.3 | 5.4 | 7.0 |
| 16.6 | 5.3 | 13.1 |
| 17.4 | 5.1 | 100.0 |
| 18.0 | 4.9 | 40.2 |
| 18.9 | 4.7 | 17.3 |
| 20.0 | 4.4 | 71.6 |
| 21.2 | 4.2 | 23.4 |
| 22.2 | 4.0 | 20.0 |
| 23.1 | 3.9 | 13.6 |
| 24.0 | 3.7 | 33.5 |
| 24.7 | 3.6 | 5.3 |
| 25.1 | 3.5 | 9.9 |
| 26.2 | 3.4 | 6.9 |
| 26.6 | 3.4 | 11.2 |
| 27.1 | 3.3 | 20.4 |
| 27.7 | 3.2 | 6.2 |
| 28.3 | 3.2 | 6.3 |
| 29.6 | 3.0 | 10.7 |
| 30.4 | 2.9 | 8.3 |
| 31.0 | 2.9 | 3.4 |
| 31.6 | 2.8 | 2.8 |
| 32.4 | 2.8 | 18.6 |
| 32.8 | 2.7 | 7.4 |
| 33.6 | 2.7 | 3.3 |
| 34.5 | 2.6 | 6.3 |
| 34.9 | 2.6 | 4.7 |
| 35.8 | 2.5 | 4.1 |
| 36.3 | 2.5 | 7.5 |
| 36.8 | 2.4 | 4.3 |
| 37.3 | 2.4 | 5.7 |
| 38.3 | 2.4 | 6.3 |
| 38.9 | 2.3 | 4.3 |

Table II sets forth the 2θ, d-spacings and relative intensities and peak locations for the powder x-ray diffraction pattern representative for the citrate salt. The numbers as listed are computer-generated.

TABLE II

Powder X-ray Diffraction Intensities and Peak Locations Representative of the Citrate Salt.

| Angle 2θ | d-value (Å) | I (rel.) |
|---|---|---|
| 13.0 | 6.8 | 14.5 |
| 17.4 | 5.1 | 100.0 |
| 18.0 | 4.9 | 40.2 |
| 18.9 | 4.7 | 17.3 |
| 20.0 | 4.4 | 71.6 |
| 21.2 | 4.2 | 23.4 |
| 22.2 | 4.0 | 20.0 |
| 24.0 | 3.7 | 33.5 |
| 27.1 | 3.3 | 20.4 |
| 32.4 | 2.8 | 18.6 |

Single Crystal X-Ray Analysis

A single crystal for the citrate salt of the invention was obtained and investigated by x-ray diffraction. A representative crystal was surveyed and a 1 Å data set (maximum sin Θ/λ=0.5) was collected on a Siemens R4RA/v diffractometer. Atomic scattering factors were taken from the *International Tables for X-Ray Crystallography*, Vol. IV, pp. 55, 99, 149 (Birmingham: Kynoch Press, 1974) From the data gathered on the single crystal, a powder X-ray diffraction pattern was calculated to offer comparison against the actual measured diffraction pattern.

Structures were solved using direct methods. The SHELXTL™ computer library provided by Bruker AXS, Inc facilitated all necessary crystallographic computations and molecular displays (SHELXTL™ Reference Manual, Version 5.1, Bruker AXS, Madison, Wis. 1997). Pertinent crystal, data collection, and refinement are summarized in Table III.

Figure 4:
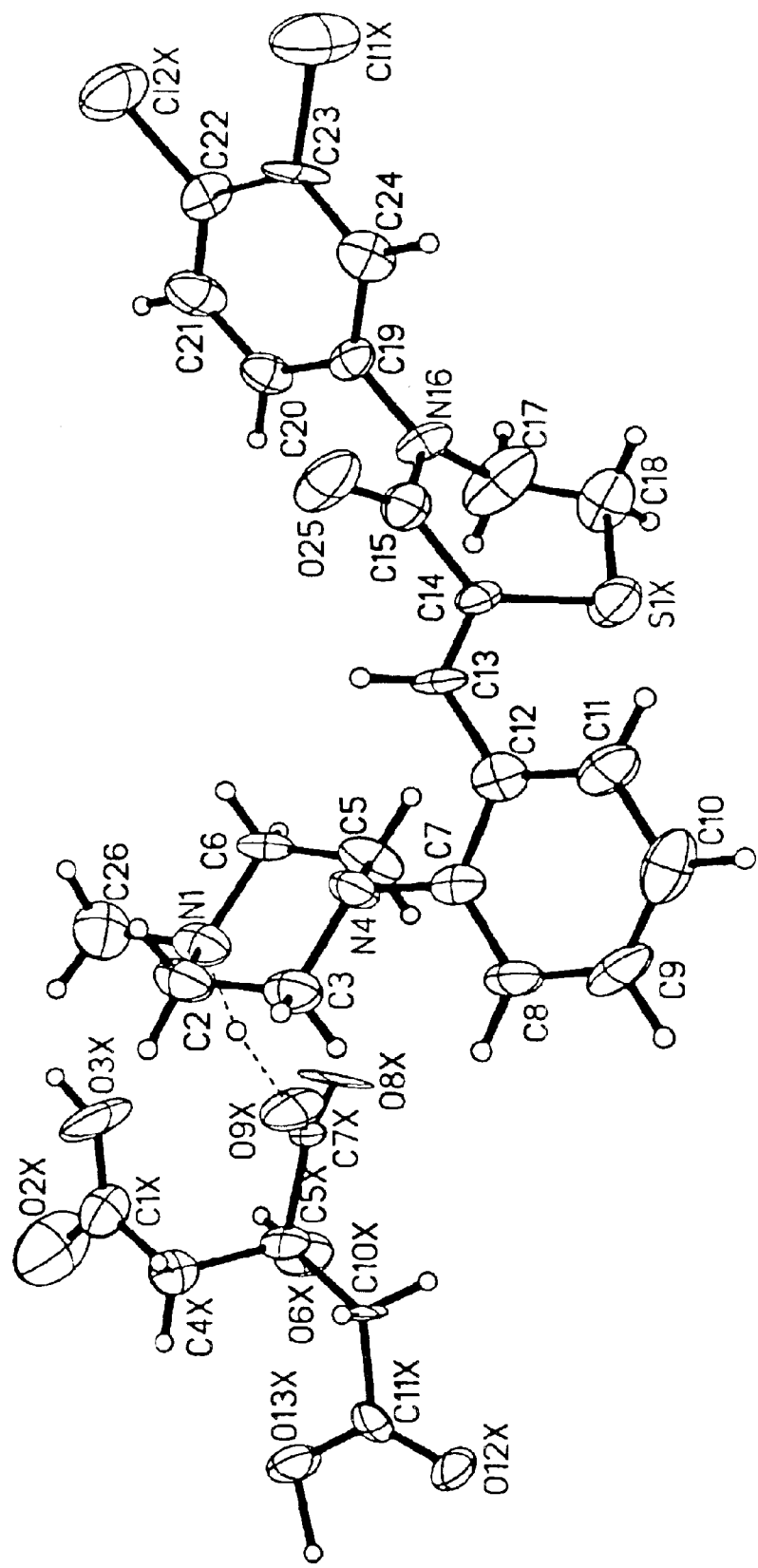
FIG. 4 is the X-ray crystal structure of the citrate salt of 4-(3,4-dichlorophenyl)-2-[2-(4-methylpiperazin-1-yl)-benzylidene]-thiomorpholin-3-one.

A trial structure was obtained by direct methods and was then refined routinely. Hydrogen positions were calculated wherever possible. The methyl hydrogens and the hydrogens on nitrogen and oxygen were located by difference Fourier techniques. The hydrogen parameters were added to the structure factor calculations but were not refined. The shifts calculated in the final cycles of least squares refinement were all less than 0.1 of the corresponding standard deviations. The final R-index was 4.72%. A final difference Fourier revealed no missing or misplaced electron density. The refined structure was plotted using the SHELXTL™ plotting package and is shown in FIG. 4.

Table IV sets forth the atomic coordinates ($\times 10^4$) and equivalent isotropic displacement parameters ($\text{Å}^2 \times 10^3$) for the salt. Table V lists the observed bond lengths [Å] and angles [°] for the citrate salt. In Table VI, the anisotropic displacement parameters ($\text{Å}^2 \times 10^3$) for the citrate salt are set forth to allow calculation of the anisotropic displacement factor exponent which has the form: $-2\pi^2[h^2 a^{*2} U_{11} + \ldots + 2h\, k\, a^* b^* U_{12}]$. Finally, in Table VII, below, hydrogen coordinates ($\times 10^4$) and isotropic displacement parameters ($\text{Å}^2 \times 10^3$) for the salt are listed.

TABLE III

Crystal Structure Data And Measurement Parameters For The Citrate Salt

| Parameter | For Citrate Salt | |
|---|---|---|
| Empirical formula | $C_{22}H_{24}N_3OSCl_2{}^+ C_6H_7O_7{}^-$ | |
| Formula weight | 640.52 | |
| Temperature | 293(2) K | |
| Wavelength | 1.54178 Å | |
| Crystal system | Monoclinic | |
| Space group | Pc | |
| Unit cell dimensions | a = 6.5940(10) Å | α = 90°. |
| | b = 15.257(2) Å | β = 101.440(10)°. |
| | c = 15.099(2) Å | γ = 90°. |
| Volume | 1488.9(4) Å$^3$ | |
| Z | 2 | |
| Density (calculated) | 1.429 Mg/m$^3$ | |
| Absorption coefficient | 3.081 mm$^{-1}$ | |
| F(000) | 668 | |
| Crystal size | 0.24 × 0.04 × 0.04 mm$^3$ | |
| Reflections collected | 1707 | |
| Independent reflections | 1707 [R(int) 0.0000] | |
| Completeness to theta = 49.98° | 100.0% | |
| Absorption correction | None | |
| Refinement method | Full-matrix least-squares on F$^2$ | |
| Data/restraints/parameters | 1707/0/391 | |
| Goodness-of-fit on F$^2$ | 1.065 | |
| Final R indices [I > 2sigma(I)] | R1 = 0.0472, wR2 = 0.1028 | |
| Absolute structure parameter | −0.01(3) | |
| Extinction coefficient | 0.0038(6) | |
| Largest diff. peak and hole | 0.223 and −0.268 e.Å$^{-3}$ | |

TABLE IV

Atomic coordinates (×10⁴) And Equivalent Isotropic Displacement Parameters ($Å^2 \times 10^3$) For The Citrate Salt. (U(eq) is defined as one third of the trace of the orthogonalized $U_{ij}$ tensor.)

| | x | y | x | U(eq) |
|---|---|---|---|---|
| S(1X) | 1600 | 3502(2) | 8401 | 53(1) |
| Cl(1X) | 7950(8) | 4063(2) | 13244(3) | 83(1) |
| Cl(2X) | 11404(8) | 2613(2) | 13403(3) | 73(1) |
| N(1) | 8720(15) | 1936(5) | 6037(6) | 42(2) |
| C(2) | 9164(19) | 2836(7) | 5723(7) | 50(3) |
| C(3) | 7216(19) | 3358(7) | 5475(7) | 48(3) |
| N(4) | 6189(14) | 3417(5) | 6246(5) | 37(2) |
| C(5) | 5665(19) | 2527(6) | 6513(7) | 44(3) |
| C(6) | 7568(18) | 1994(7) | 6786(6) | 41(3) |
| C(7) | 4480(17) | 4015(6) | 6160(7) | 34(3) |
| C(8) | 3464(19) | 4335(7) | 5318(7) | 45(3) |
| C(9) | 1780(20) | 4884(8) | 5270(8) | 57(4) |
| C(10) | 1145(19) | 5140(7) | 6041(9) | 55(3) |
| C(11) | 2141(19) | 4849(7) | 6862(7) | 47(3) |
| C(12) | 3874(17) | 4282(6) | 6954(6) | 36(3) |
| C(13) | 5020(16) | 4044(6) | 7850(6) | 35(3) |
| C(14) | 4255(15) | 3731(6) | 8528(6) | 32(3) |
| C(15) | 5686(18) | 3625(7) | 9400(7) | 41(3) |
| N(16) | 5221(14) | 3032(5) | 10007(5) | 38(2) |
| C(17) | 3520(20) | 2409(8) | 9721(10) | 77(4) |
| C(18) | 1591(19) | 2834(8) | 9378(8) | 58(3) |
| C(19) | 6643(17) | 2904(7) | 10837(6) | 33(3) |
| C(20) | 8123(17) | 2257(7) | 10928(7) | 40(3) |
| C(21) | 9521(19) | 2151(7) | 11710(7) | 51(3) |
| C(22) | 9542(18) | 2713(7) | 12428(7) | 45(3) |
| C(23) | 8029(19) | 3353(7) | 12367(6) | 43(3) |
| C(24) | 6611(19) | 3453(7) | 11563(7) | 45(3) |
| O(25) | 7262(14) | 4069(6) | 9602(5) | 70(3) |
| C(26) | 10622(18) | 1388(7) | 6296(8) | 57(3) |
| C(1X) | 10057(19) | −243(7) | 3822(8) | 53(3) |
| O(2X) | 11060(17) | −820(6) | 3541(6) | 100(4) |
| O(3X) | 10378(16) | −38(6) | 4658(6) | 84(3) |
| O(4X) | 8610(18) | 320(6) | 3209(6) | 40(3) |
| O(5X) | 6358(19) | 214(6) | 3317(7) | 35(3) |
| O(6X) | 5754(14) | −675(5) | 3152(5) | 52(2) |
| C(7X) | 6105(16) | 491(8) | 4257(6) | 39(3) |
| O(8X) | 5421(15) | −95(6) | 4709(6) | 75(3) |
| O(9X) | 6600(14) | 1254(5) | 4507(5) | 55(2) |
| C(10X) | 4897(18) | 794(7) | 2640(6) | 46(3) |
| C(11X) | 4463(19) | 533(6) | 1651(6) | 32(2) |
| O(12X) | 2826(13) | 708(5) | 1170(5) | 50(2) |
| O(13X) | 5938(13) | 140(6) | 1372(5) | 64(3) |

TABLE V

Observed Bond Lengths [Å] And Angles [°] For Citrate Salt.

| | | | |
|---|---|---|---|
| S(1X)-C(14) | 1.758(10) | C(15)-N(16) | 1.365(12) |
| S(1X)-C(18) | 1.794(11) | N(16)-C(19) | 1.422(12) |
| Cl(1X)-C(23) | 1.719(10) | N(16)-C(17) | 1.470(13) |
| Cl(2X)-C(22) | 1.727(10) | C(17)-C(18) | 1.429(17) |
| N(1)-C(6) | 1.486(12) | C(19)-C(20) | 1.375(13) |
| N(1)-C(2) | 1.500(12) | C(19)-C(24) | 1.385(14) |
| N(1)-C(26) | 1.493(13) | C(20)-C(21) | 1.356(14) |
| C(2)-C(3) | 1.495(16) | C(21)-C(22) | 1.380(14) |
| C(3)-N(4) | 1.461(12) | C(22)-C(23) | 1.386(14) |
| N(4)-C(7) | 1.435(13) | C(23)-C(24) | 1.386(14) |
| N(4)-C(5) | 1.478(12) | C(1X)-O(2X) | 1.227(13) |
| C(5)-C(6) | 1.483(14) | C(1X)-O(3X) | 1.278(13) |
| C(7)-C(8) | 1.402(13) | C(1X)-C(4X) | 1.468(14) |
| C(7)-C(12) | 1.398(13) | C(4X)-C(5X) | 1.534(15) |
| C(8)-C(9) | 1.384(16) | C(5X)-O(6X) | 1.423(11) |
| C(9)-C(10) | 1.369(15) | C(5X)-C(7X) | 1.522(14) |
| C(10)-C(11) | 1.357(14) | C(5X)-C(10X) | 1.537(14) |
| C(11)-C(12) | 1.418(15) | C(7X)-O(9X) | 1.247(12) |
| C(12)-C(13) | 1.458(13) | C(7X)-O(8X) | 1.261(12) |
| C(13)-C(14) | 1.317(12) | C(10X)-C(11X) | 1.517(13) |
| C(14)-C(15) | 1.470(14) | C(11X)-O(12X) | 1.205(11) |
| C(15)-O(25) | 1.227(12) | C(11X)-O(13X) | 1.283(11) |
| C(14)-S(1X)-C(18) | 100.9(5) | C(18)-C(17)-N(16) | 112.7(10) |
| C(6)-N(1)-C(2) | 110.3(8) | C(17)-C(18)-S(1X) | 114.1(9) |
| C(6)-N(1)-C(26) | 111.3(8) | C(20)-C(19)-C(24) | 118.5(9) |
| C(2)-N(1)-C(26) | 112.9(9) | C(20)-C(19)-N(16) | 121.2(9) |
| N(1)-C(2)-C(3) | 110.8(9) | C(24)-C(19)-N(16) | 120.3(9) |
| N(4)-C(3)-C(2) | 110.2(8) | C(21)-C(20)-C(19) | 121.3(10) |
| C(7)-N(4)-C(3) | 116.6(8) | C(20)-C(21)-C(22) | 120.6(10) |
| C(7)-N(4)-C(5) | 112.8(8) | C(21)-C(22)-C(23) | 119.4(10) |
| C(3)-N(4)-C(5) | 109.3(8) | C(21)-C(22)-Cl(2X) | 120.6(9) |
| N(4)-C(5)-C(6) | 110.4(9) | C(23)-C(22)-Cl(2X) | 119.9(8) |
| C(5)-C(6)-N(1) | 110.7(8) | C(24)-C(23)-C(22) | 119.2(9) |
| C(8)-C(7)-C(12) | 120.7(10) | C(24)-C(23)-Cl(1X) | 119.1(9) |
| C(8)-C(7)-N(4) | 121.9(9) | C(22)-C(23)-Cl(1X) | 121.6(8) |
| C(12)-C(7)-N(4) | 117.4(8) | C(23)-C(24)-C(19) | 120.9(10) |
| C(9)-C(8)-C(7) | 119.6(10) | O(2X)-C(1X)-C(3X) | 121.5(11) |
| C(10)-C(9)-C(8) | 120.3(10) | O(2X)-C(1X)-C(4X) | 122.0(11) |
| C(11)-C(10)-C(9) | 120.6(11) | O(3X)-C(1X)-C(4X) | 116.1(10) |
| C(10)-C(11)-C(12) | 121.6(11) | C(1X)-C(4X)-C(5X) | 113.2(9) |
| C(7)-C(12)-C(11) | 117.1(9) | O(6X)-C(5X)-C(7X) | 110.4(9) |
| C(7)-C(12)-C(13) | 122.6(10) | O(6X)-C(5X)-C(4X) | 109.0(8) |
| C(11)-C(12)-C(13) | 120.2(9) | C(7X)-C(5X)-C(4X) | 110.9(8) |
| C(14)-C(13)-C(12) | 127.1(9) | O(6X)-C(5X)-C(10X) | 108.4(8) |
| C(13)-C(14)-C(15) | 117.4(9) | C(7X)-C(5X)-C(10X) | 106.9(8) |
| C(13)-C(14)-S(1X) | 120.9(7) | C(4X)-C(5X)-C(10X) | 111.1(8) |
| C(15)-C(14)-S(1X) | 121.6(8) | O(9X)-C(7X)-O(8X) | 126.8(9) |
| O(25)-C(15)-N(16) | 119.5(9) | O(9X)-C(7X)-C(5X) | 118.0(10) |
| O(25)-C(15)-C(14) | 121.5(10) | O(8X)-C(7X)-C(5X) | 115.2(10) |
| N(16)-C(15)-C(14) | 119.0(10) | C(11X)-C(10X)-C(5X) | 118.4(8) |
| C(15)-N(16)-C(19) | 119.1(9) | O(12X)-C(11X)-O(13X) | 123.6(9) |
| C(15)-N(16)-C(17) | 119.5(9) | O(12X)-C(11X)-C(10X) | 120.4(9) |
| C(19)-N(16)-C(17) | 120.1(9) | O(13X)-C(11X)-C(10X) | 116.0(9) |

TABLE VI

Anisotropic displacement parameters ($Å^2 \times 10^3$) for Citrate Salt. The anisotropic displacement factor exponent takes the form:
$-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| S(1X) | 40(2) | 76(2) | 39(2) | 6(2) | 2(1) | −14(2) |
| Cl(1X) | 128(3) | 69(2) | 46(2) | −17(2) | 1(2) | 24(2) |
| Cl(2X) | 81(2) | 82(2) | 47(2) | 7(2) | −13(2) | 13(2) |
| N(1) | 53(6) | 44(6) | 30(5) | −11(4) | 10(5) | −16(5) |
| C(2) | 53(8) | 57(8) | 46(7) | −9(6) | 28(6) | −22(7) |
| C(3) | 56(8) | 56(7) | 35(6) | 1(5) | 16(6) | −14(6) |
| N(4) | 45(6) | 45(6) | 23(5) | −1(4) | 12(4) | −2(5) |
| C(5) | 61(8) | 39(6) | 36(6) | 15(5) | 24(6) | −7(6) |
| C(6) | 63(8) | 41(6) | 22(6) | 2(5) | 17(6) | −2(6) |
| C(7) | 43(7) | 37(6) | 21(6) | 3(5) | 4(5) | −23(6) |
| C(8) | 51(8) | 49(7) | 33(7) | 6(5) | 6(6) | −15(7) |
| C(9) | 64(10) | 52(7) | 45(8) | 22(6) | −15(7) | −17(8) |
| C(10) | 49(9) | 43(7) | 66(9) | 11(7) | −5(7) | −1(6) |
| C(11) | 55(8) | 46(7) | 36(7) | 10(5) | −1(6) | 4(6) |
| C(12) | 47(7) | 27(6) | 33(7) | 6(5) | 5(5) | −9(5) |
| C(13) | 38(7) | 43(6) | 24(6) | 0(5) | 6(5) | −4(5) |
| C(14) | 35(6) | 39(6) | 19(5) | −6(5) | 2(5) | −12(5) |
| C(15) | 35(7) | 51(7) | 38(7) | −5(6) | 5(6) | −8(6) |
| N(16) | 53(6) | 28(5) | 30(5) | 6(4) | −1(5) | −8(5) |
| C(17) | 77(10) | 58(8) | 78(9) | 22(7) | −26(8) | −39(8) |
| C(18) | 46(8) | 56(8) | 71(8) | 18(7) | 7(7) | −22(7) |
| C(19) | 39(7) | 35(6) | 22(6) | 5(5) | −2(5) | −1(6) |
| C(20) | 51(8) | 41(7) | 29(6) | −1(5) | 9(6) | 7(6) |
| C(21) | 61(8) | 50(7) | 45(7) | 10(6) | 22(7) | 19(6) |
| C(22) | 49(8) | 45(7) | 39(7) | 18(6) | 3(6) | 19(6) |
| C(23) | 70(8) | 47(7) | 14(6) | −2(5) | 12(6) | 1(7) |
| C(24) | 60(9) | 35(7) | 41(7) | −2(6) | 13(7) | 1(6) |
| O(25) | 60(6) | 104(7) | 39(4) | 29(4) | −6(4) | −35(6) |
| C(26) | 57(9) | 55(7) | 60(8) | −12(6) | 14(7) | 2(7) |
| C(1X) | 54(8) | 41(7) | 61(9) | −9(6) | 2(7) | 4(7) |
| O(2X) | 106(9) | 93(7) | 87(7) | −21(6) | −13(6) | 43(7) |
| O(3X) | 99(8) | 107(7) | 33(5) | −7(5) | −21(5) | 52(6) |
| C(4X) | 53(8) | 30(6) | 34(6) | −1(5) | 4(6) | 14(6) |
| C(5X) | 49(8) | 31(6) | 24(5) | 1(5) | 7(5) | 3(6) |
| O(6X) | 71(6) | 43(5) | 40(5) | −4(3) | 8(4) | −5(4) |

TABLE VI-continued

Anisotropic displacement parameters (Å² × 10³) for Citate Salt. The anisotropic displacement factor exponent takes the form:
$-2\pi^2[h^2 a^{*2}U_{11} + \ldots + 2 h k a^* b^* U_{12}]$

|  | $U_{11}$ | $U_{22}$ | $U_{33}$ | $U_{23}$ | $U_{13}$ | $U_{12}$ |
|---|---|---|---|---|---|---|
| C(7X) | 38(7) | 62(8) | 15(6) | −7(6) | −2(5) | 9(6) |
| O(8X) | 106(8) | 108(7) | 18(4) | −7(4) | 29(5) | −51(6) |
| O(9X) | 75(6) | 51(5) | 34(4) | −18(4) | 0(4) | 10(5) |
| C(10X) | 54(8) | 60(7) | 23(6) | −4(5) | 9(5) | 18(6) |
| C(11X) | 40(7) | 33(6) | 27(6) | 10(5) | 13(6) | 6(6) |
| O(12X) | 43(5) | 75(5) | 28(4) | −12(4) | −7(4) | 15(4) |
| O(13X) | 68(6) | 104(7) | 19(4) | 9(4) | 5(4) | 44(5) |

TABLE VII

Hydrogen coordinates (×10⁴) and Isotropic Displacement Parameters (Å² × 10³) for the Citrate Salt.

|  | x | y | z | U(eq) |
|---|---|---|---|---|
| H(1X) | 7880(190) | 1710(70) | 5570(80) | 80 |
| H(2A) | 9814 | 2789 | 5202 | 80 |
| H(2B) | 10118 | 3134 | 6199 | 80 |
| H(3A) | 7538 | 3942 | 5290 | 80 |
| H(3B) | 6298 | 3082 | 4971 | 80 |
| H(5A) | 4753 | 2246 | 6011 | 80 |
| H(5B) | 4944 | 2564 | 7013 | 80 |
| H(6A) | 7199 | 1410 | 6952 | 80 |
| H(6B) | 8445 | 2258 | 7310 | 80 |
| H(8) | 3923 | 4179 | 4796 | 80 |
| H(9) | 1065 | 5080 | 4711 | 80 |
| H(10) | 23 | 5518 | 6002 | 80 |
| H(11) | 1675 | 5026 | 7377 | 80 |
| H(13) | 6447 | 4120 | 7953 | 80 |
| H(17A) | 3859 | 2028 | 9257 | 80 |
| H(17B) | 3373 | 2045 | 10232 | 80 |
| H(18A) | 1235 | 3198 | 9851 | 80 |
| H(18B) | 524 | 2391 | 9226 | 80 |
| H(20) | 8167 | 1886 | 10444 | 80 |
| H(21) | 10473 | 1695 | 11764 | 80 |
| H(24) | 5623 | 3895 | 11512 | 80 |
| H(26A) | 11422 | 1595 | 6859 | 80 |
| H(26B) | 11432 | 1429 | 5835 | 80 |
| H(26C) | 10234 | 789 | 6361 | 80 |
| H(3XX) | 11700(300) | −220(100) | 5150(100) | 140(60) |
| H(4XA) | 8699 | 184 | 2591 | 80 |
| H(4XB) | 9020 | 927 | 3321 | 80 |
| H(6XX) | 6600(200) | −1000(80) | 3490(80) | 80 |
| H(10A) | 3582 | 822 | 2834 | 80 |
| H(10B) | 5465 | 1382 | 2683 | 80 |
| H(13X) | 5480(180) | 190(70) | 610(80) | 80 |

Figure 3:
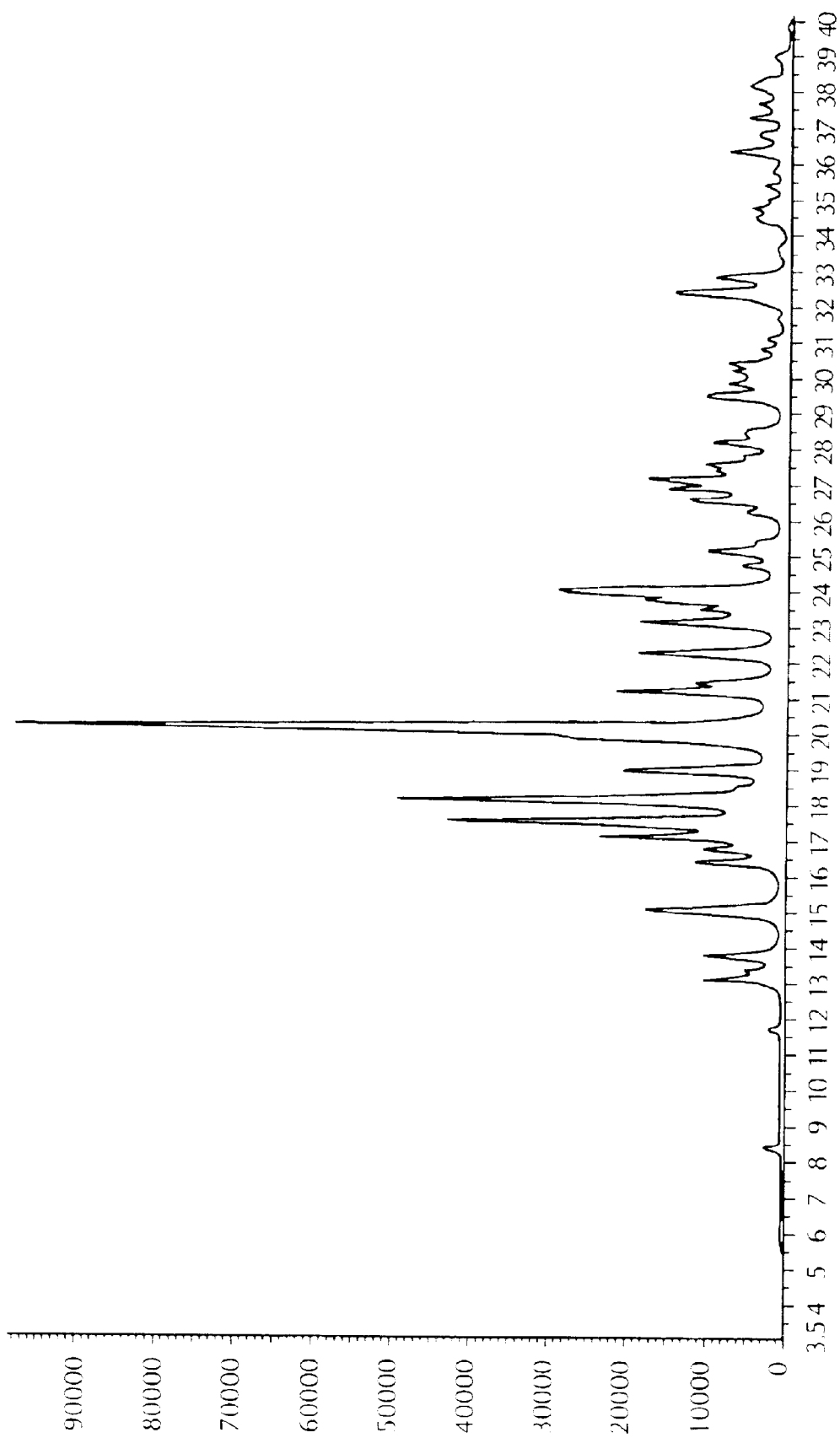
FIG. 3 is the calculated powder X-ray diffraction pattern of the citrate salt of 4-(3,4-dichlorophenyl)-2-[2-(4-methylpiperazin-1-yl)-benzylidene]-thiomorpholin-3-one (y axis is linear counts per second; X in degrees 2 theta).

The powder X-ray diffraction pattern was calculated from the single crystal data gathered for the citrate salt via the use of the XFOG and XPOW computer programs provided as part of the SHELXTL™ computer library. The calculated powder pattern is shown in FIG. 3.

Solid State NMR

The citrate salt was characterized by solid state NMR techniques. Approximately 300 mg of a sample was tightly packed into 7 mm ZrO spinner. The $^{13}$C NMR spectra were collected using cross-polarization magic angle spinning (CPMAS) at 295 K on Bruker 7 mm WB MAS probe positioned into a wide-bore Bruker Avance DRX 500 MHz NMR spectrometer. The sample was spun at 15.0 kHz. The cross-polarization contact time was set to 1 ms. The total of 512 scans were acquired for most of the samples resulting in approximately 30 minute acquisition times. The spectra were referenced using external sample of adamantane (δ 29.5 ppm) with the most upfield methyl signal set to 29.5 ppm.

Figure 5:
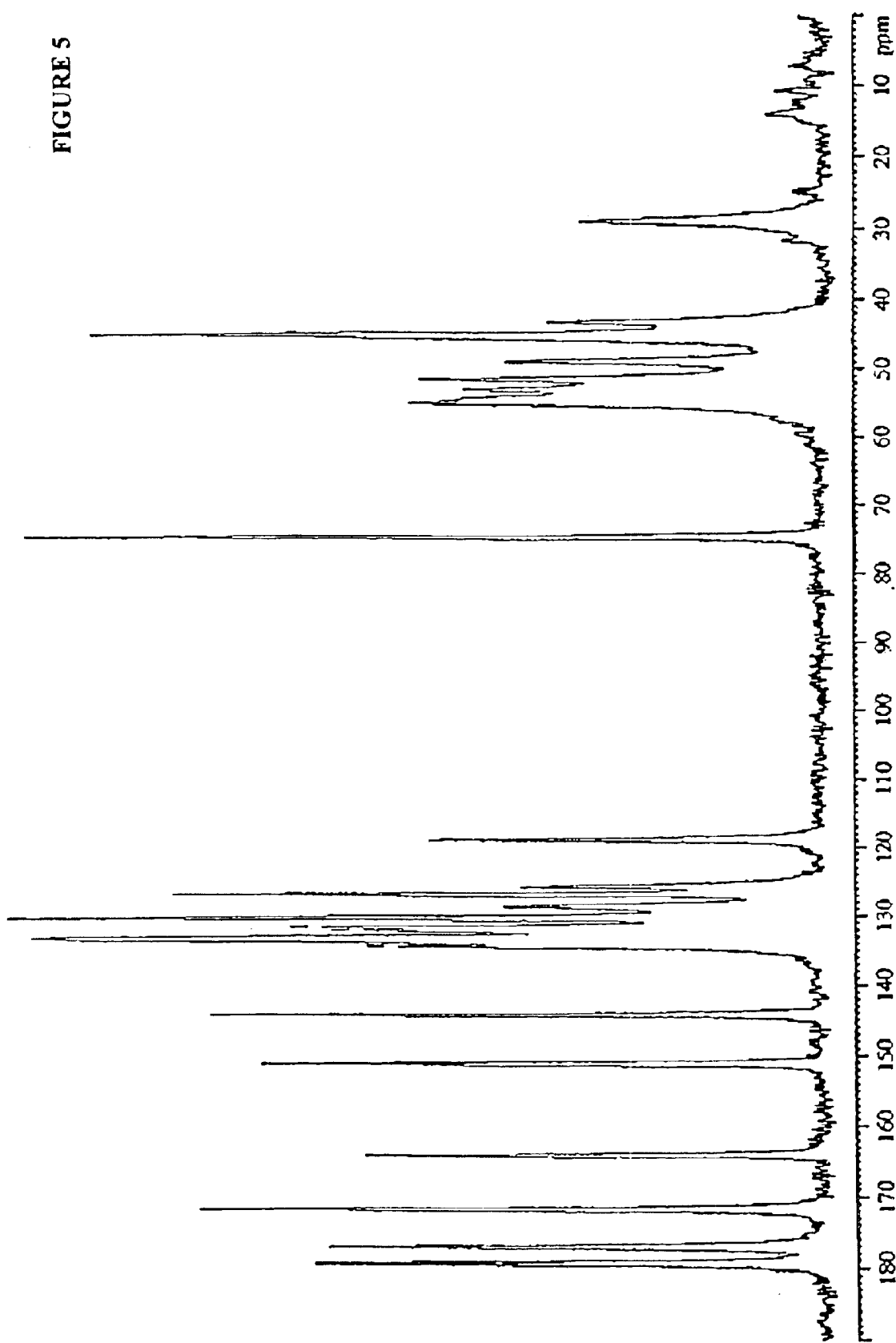
FIG. 5 is the $^{13}$C NMR spectrum of the citrate salt of 4-(3,4-dichlorophenyl)-2-[2-(4-methylpiperazin-1-yl)-benzylidene]-thiomorpholin-3-one in the solid phase as measured by cross-polarization magic angle spinning (CPMAS) at 295 K on a Bruker 7 mm wide-bore magic angle spinning (WB MAS) probe positioned in a Bruker Avance DRX 500 MHz NMR Spectrometer.

The resulting $^{13}$C NMR CPMAS spectrum for the citrate salt is shown in FIG. 5. The samples of the citrate salt behaved reasonably well from the point of view of solid state spectra quality. The resolution was good and the sensitivity was acceptable.

The major resonance peaks for the solid state carbon spectrum of the citrate salt of 4-(3,4-dichlorophenyl)-2-[2-(4-methylpiperazin-1-yl)-benzylidene]-thiomorpholin-3-one downfield from 100 ppm are listed in Table VIII.

TABLE VIII

The Major Solid State $^{13}$C-NMR Resonance Peaks For Citrate Salt (adamantane standard 29.5 ppm).

| $^{13}$C (ppm) |
|---|
| 179.3 |
| 177.0 |
| 171.6 |
| 164.0 |
| 151.0 |
| 144.1 |

The citrate salt of the invention (hereafter "the active salt") can be administered via either the oral, transdermal (e.g., through the use of a patch), intranasal, sublingual, rectal, parenteral or topical routes. Transdermal and oral administration are preferred. The active salt is, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active salt can be administered alone or in combination with pharmaceutically acceptable carriers or diluents by any of the several routes previously indicated. More particularly, the active salt can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active salt is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active salt topically and this can be done by way of creams, a patch, jellies, gels, pastes, ointments and the like, in accordance with standard pharmaceutical practice.

EXAMPLE

The following example illustrate the method and compound of the present invention. It will be understood, however, that the invention is not limited to this specific Example.

Citrate Salt of 4-(3,4-Dichlorophenyl)-2-[2-(4-methylpiperazin-1-yl)-benzylidene]-thiomorpholin-3-one In a 1-liter round-bottomed flask equipped with an overhead mechanical stirrer, the free base of 4-(3,4-dichlorophenyl)-2-[2-(4-methylpiperazin-1-yl)-benzylidene]-thiomorpholin-3-one (30.14 g; 0.067 mol; prepared in accordance with the procedures set forth in International Patent Publication No. WO 98/14433) was dissolved in 525 ml 2-propanol. The solution was stirred and heated to 50° C. Citric acid (16.2 g; 0.084 mol) was added in portions to the resulting clear solution and the reaction mixture was allowed to cool and was granulated at room temperature for 18 hours. A sample of the precipitated solid was examined by DSC to ascertain whether any unreacted free base were present prior to collection of the white crystalline solid product. After filtration, the solid product was washed with 2-propanol (100 ml) and dried at 45° C. under vacuum with a nitrogen purge. The title citrate salt was yielded in 94% yield (40.6 g; 0.063 mol).

What is claimed is:

1. The citrate salt of 4-(3,4-dichlorophenyl)-2-[2-(4-methylpiperazin-1-yl)-benzylidene]-thiomorpholin-3-one wherein 4-(3,4-dichlorophenyl)-2-[2-(4-methylpiperazin-1-yl)-benzylidene]-thiomorpholin-3-one is represented by the formula

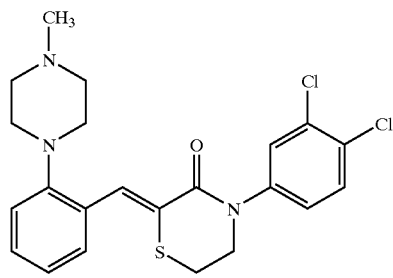

said citrate salt characterized by at least one of the following: an x-ray diffraction pattern characterized substantially by an x-ray diffraction pattern peak as measured with copper radiation of a 2θ of about 13.0 or about 7.4 or about 18.0 or about 18.9 or about 20.0 or about 21.2 or about 22.2 or about 24.0 or about 27.1 or about 32.4; an onset of melting/descomposition transition at 198–199° C.; or a principal resonance peak of δ 179.3 or δ 177.0 or δ 171.6 or δ 164.0, or δ 151.0 or δ 144.1 when examined by solid state $^{13}$C NMR cross-polarization magic angle spinning techniques.

2. A pharmaceutical composition comprising a compound according to claim 1 and a pharmaceutically acceptable carrier.

3. A method of treating depression in a mammal comprising administering to the subject in need of treatment a therapeutically effective amount of a compound according to claim 1.

* * * * *